United States Patent [19] [11] 3,966,793
Schmitt, deceased [45] June 29, 1976

[54] INTERMEDIATES FOR PREPARING 1,4-BENZODIAZEPINE-2-ONES HAVING A CARBOXYLIC ACID ESTER OR AMIDE GROUP IN THE 3-POSITION

[75] Inventor: Josef Schmitt, deceased, late of L'Hay-les-Roses, France, by Marcelle Armande Georgette Schmitt, administratrix

[73] Assignee: Clin Midy, Paris, France
[22] Filed: Sept. 26, 1973
[21] Appl. No.: 401,029

Related U.S. Application Data

[60] Continuation-in-part of Ser. No. 739,990, Feb. 19, 1968, abandoned, which is a division of Ser. No. 463,613, June 14, 1965, abandoned.

[30] Foreign Application Priority Data
June 15, 1964 France ............ 64.978360
Apr. 12, 1965 France ............ 65.12886

[52] U.S. Cl. .......... 260/471 A; 260/239.3 D; 260/329 AM; 260/332.2 A; 260/332.3 R; 260/332.5; 260/347.4; 260/347.7; 260/518 R; 260/519; 260/566 D; 260/566 R; 424/275; 424/285; 424/309
[51] Int. Cl.² ................... C07C 119/00
[58] Field of Search ............... 260/471 A

[56] References Cited
UNITED STATES PATENTS
3,751,466 8/1973 Menasse et al. ............ 260/471 A Primary Examiner—James A. Patten
Attorney, Agent, or Firm—Stevens, Davis, Miller & Mosher

[57] ABSTRACT
Intermediates for preparing novel benzodiazepines having the formula

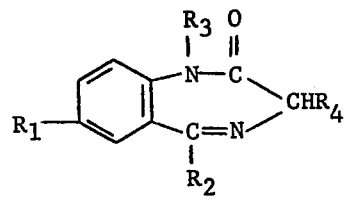

in which $R_1$ is a hydrogen or halogen atom or a trifluoromethyl, loweralkyl, loweralkoxy, nitro or amino group; $R_2$ is a furyl, a thienyl, cyclohexyl, a loweralkyl group or a phenyl group which may be substituted by a halogen atom or by a trifluoromethyl, nitro, loweralkoxy or loweralkyl group; and $R_3$ is a hydrogen atom or a loweralkyl group; and $R_4$ is lowercarbalkoxy, carbamoyl, N-loweralkylcarbamoyl, N,N-diloweralkylcarbamoyl, N-(diloweralkylaminoalkyl)carbamoyl, a group having the formula —COOCat in which Cat is a cation of an alkali metal or a semication of an alkaline earth metal or COOCat.CatOH, said intermediates being ortho-aminoaryl ketimines having the formula

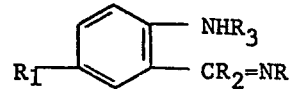

wherein R is hydrogen or

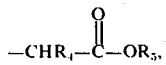

$R_1$, $R_2$, and $R_3$ are as defined above, $R_4$ is a hydrogen atom, a lowercarbalkoxy, carbamoyl, N-loweralkylcarbamoyl, N,N-diloweralkylcarbamoyl, N-(diloweralkylaminoalkyl)-carbamoyl, alkyl or substituted alkyl group; and $R_5$ is a loweralkyl group.

13 Claims, No Drawings

INTERMEDIATES FOR PREPARING 1,4-BENZODIAZEPINE-2-ONES HAVING A CARBOXYLIC ACID ESTER OR AMIDE GROUP IN THE 3-POSITION

CROSS REFERENCE TO RELATED APPLICATIONS

This application is a continuation-in-part of co-pending application Ser. No. 739,990, filed Feb. 19, 1968, which is a division of application, Ser. No. 463,613 filed June 14, 1965, both now abandoned.

This invention relates to intermediates useful in preparing certain benzodiazepines which are useful as neurotropic agents, and more particularly relates to orthoaminoarylketimines which are useful in preparing certain benzodiazepines such as 7-chloro-2,3-dihydro-2-oxo-5-phenyl-1H-benzo[f]-1,4-diazepine-3-carboxylic acid, monopotassium salt, monopotassium hydroxide, as well as intermediate benzodiazepines which are also useful for the preparation of the final products.

The ortho-aminoarylketimines are represented by the general formula

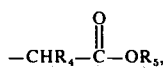

wherein R is hydrogen or

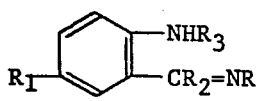

$R_1$ is a hydrogen or halogen atom or a trifluoromethyl, loweralkyl, loweralkoxy, nitro or amino group, $R_2$ is a furyl, a thienyl, a cyclohexyl, a loweralkyl or a phenyl group which may be substituted by a halogen atom or by a trifluoromethyl, nitro, loweralkoxy or loweralkyl group; $R_3$ is a hydrogen atom or a loweralkyl group, $R_4$ is a hydrogen atom, a lowercarbalkoxy, carbamoyl, N-loweralkylcarbamoyl, N,N-diloweralkylcarbamoyl, N-(diloweralkylaminoalkyl)carbamoyl, alkyl or substituted alkyl group; and $R_5$ is a loweralkyl group.

The preferred ketimines are represented by the formula

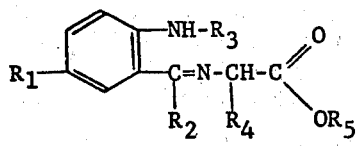    I wherein $R_1$ is chloro, hydrogen or methyl; $R_2$ is phenyl or n-butyl; $R_3$ is hydrogen or methyl; $R_4$ is hydrogen or $COOC_2H_5$ and $R_5$ is ethyl.

The diazepine intermediates are represented by the formula

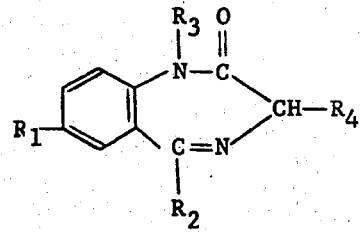    II wherein $R_1$ is chloro, hydrogen, methyl, nitro or amino; $R_2$ is benzyl or cyclohexyl; $R_3$ is hydrogen or methyl; and $R_4$ is hydrogen or $COR_6$ wherein $R_6$ is loweralkoxy or

with $R_7$ and $R_8$ being the same or different members of the group consisting of hydrogen, loweralkyl or lowerdialkylaminoalkyl.

The final products, which are substituted benzodiazepines, are represented by the general formula

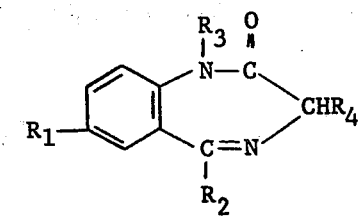

in which $R_1$, $R_2$ and $R_3$ are as defined above and $R_4$ is a lowercarbalkoxy, a carbamoyl, an N-loweralkylcarbamoyl, an N,N-diloweralkylcarbamoyl, an N(diloweralkylaminoalkyl)-carbamoyl, a group having the general formula —COOOCat in which Cat is a cation of an alkali metal or a semication of an alkaline earth metal or a group which, in a naturally occurring α-aminocarboxylic acid, is linked to the carbon atom carrying the α-amino group.

In the case where $R_4$ is COOCat, particularly when the cation is potassium, the compounds are generally obtained as a COOCat.CatOH, that is, a salt having one molecule of CatOH in the crystal lattice. The mono salts are generally prepared from the "dimetal salts".

In the present specification, the alkyl groups, including those present in alkoxy and aralkyl groups have 1 to 7 carbon atoms in a straight or branched chain; for example, methyl, ethyl, propyl, isopropyl, butyl, isobutyl, tertiary butyl, amyl and hexyl groups.

These products corresponding to Formula I may be prepared by a reaction for which the starting material is an ortho-amino aryl ketimine represented by the general Formula III.

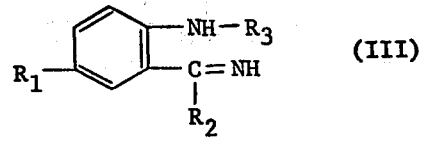    (III)

in which the groups $R_1$, $R_2$ and $R_3$ are as above defined.

These ortho-aminoaryl ketimines may be obtained according to the present invention by reacting an orthoaminobenzonitrile having the substituent $R_1$ with an excess of magnesium alkyl halide or magnesium aryl halide $R_2MgX$, in which $R_2$ is as above defined and X is a halogen atom, particularly bromine. A substantial excess of the Grignard reagent $R_2MgX$ is used, preferably about 3 to 4 molecules per molecule of ortho-aminobenzonitrile used. The process may be carried out in anhydrous ethyl ether and the starting materials allowed to react in boiling solvent for up to about 15 hours. After cooling, the magnesium complex is decomposed with an aqueous ammonium chloride solution and the solvent evaporated. The ortho-amino aryl ketimine crystallizes in most cases spontaneously and may be purified by recrystallization from a suitable solvent, in particular from a hydrocarbon such as hexane or cyclohexane.

The ortho-amino aryl ketimines are thus obtained in the form of pale yellow, well defined crystalline compounds. The yield is generally high, frequently of the order of 80 to 90%. The infrared spectra of these compounds agree with the structure indicated and are, moreover, confirmed by elementary analysis. The compounds have, amoung others, two bands characteristic of the vibrational frequency of the N—H bond: a fine line in the region of 3480 cm.$^{-1}$ (absent if the aromatic amine is secondary) and a wide band at 3270–3300 cm.$^{-1}$ due to the N—H of the imine and to the chelated NH of the $NH_2$ (or NH—R) group; moreover, the infrared spectra show two bands of vibration in the region of 1600 cm.$^{-1}$ (1610–1580 cm.$^{-1}$) due to the aromatic >C=C< conjugated to >C=N.

Table I sets out certain imines having the general Formula III which are new and which may be prepared as indicated in the examples given hereinafter.

TABLE I

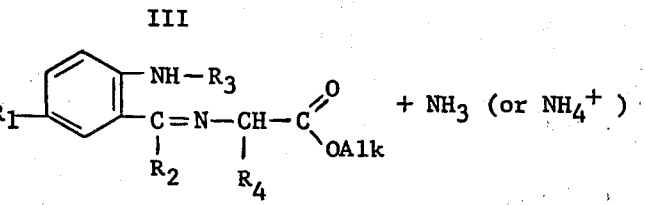

| CB No. | $R_1$ | $R_2$ | $R_3$ | Example |
|---|---|---|---|---|
| 4356 | Cl | $C_6H_5$ | H | 1 |
| 4357 | Cl | $C_6H_5$ | $CH_3$ | 2 |
| 4358 | H | $C_6H_5$ | H | 3 |
| 4359 | Cl | $C_6H_{11}$ (cyclohexyl) | H | 4 |
| 4360 | Cl | $n-C_4H_9$ | H | 5 |

The substituted imines having the general Formula I may be prepared from ortho-amino aryl ketimines (III) and an ester of an α-aminoacetic acid.

In the simplest case, this α-aminoacetic acid ester may be an ester of glycine, but it may also be an ester of a naturally occurring optically active or racemic α-amino acid such as alanine, leucine or methionine: lastly, the ester may be a derivative of aminomalonic acid, in particular dimethyl or diethyl aminomalonate.

These esters may be used in the form of bases but preferably in the form of salts which are easier to deal with than the base, especially the hydrochloride. The reaction is accompanied by liberation of ammonia, either free or combined in the form of a salt according to the equation given below (in which Alk denotes a loweralkyl group):

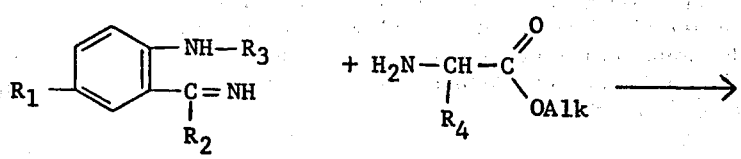

The reaction may be carried out in a solvent which is inert with respect to the imine III, in particular a lower aliphatic alcohol or a hydrocarbon such as benzene or toluene, and at a temperature between room temperature and the reflux temperature of the diluent. The reaction time may vary between 1 and 12 hours; the higher the temperature employed, the shorter will be the reaction time. In certain cases, the reaction product separates spontaneously from the alcoholic solution at room temperature. Nevertheless, it is advantageous to evaporate off the solvent when the reaction is terminated, extract the product with an inert solvent and isolate it by crystallization from a suitable solvent.

The substituted imines I which have an ester function are obtained in the form of pale yellow products, in most cases crystalline but sometimes in the form of oils. Their structure is determined by elementary analysis, study of their infrared spectra and the results of acid hydrolysis.

As could be expected theoretically, the substituted imines (I) can exist in two stereoisomeric forms, one of which, generally obtained in larger quantity, is characterized by an intramolecular N—H hydrogen bond between a hydrogen on the amino group and the nitrogen of the imino group (forming a chelate ring). In two of the appended examples (see Examples 6 and 7) these two forms were isolated by fractional crystallization; in the other cases, the product isolated was generally a crystalline product corresponding to the chelate form.

The infrared spectra, determined in methylene chloride, of the chelate forms have a vibration band of the N—H group in the region of 3480 cm.$^{-1}$ (a fine line would not be seen in the case of a secondary amine) and a wide band at 3150–3300 cm.$^{-1}$ due to the chelate bond N—H of the group $NH_2$ (or NH—R); in the region of 1730–1740 cm.$^{-1}$ a vibration band of >C=O of the ester radical; in the region of 1610–1620 cm.$^{-1}$ a band of the aromatic >C=C< (and >C=N—); at 1200–1180 cm.$^{-1}$ a C—O—C band (ester) shifted to 1220 cm.$^{-1}$ in the case of malonic esters. The non-chelate forms differ from the above by the existence of a doublet formed by two fine lines due to the N—H vibrations of $NH_2$ (a single line at 3400 cm.$^{-1}$ in the case of secondary amines) and by the absence of absorption bands between 3150 and 3300 cm.$^{-1}$.

Investigation of the hydrolysis of imines (I) by a strong mineral acid particularly hydrochloric acid leads to different results according to the presence or absence of an internal hydrogen bond; if there is no chelation, the action of hydrochloric acid leads to the formation of the corresponding ortho-amino ketone due to severing of the imine bond; in the case of internal chelation, the imino bond is is not severed and the corresponding benzodiazepine is formed, the configuration of which is moreover favorable to cyclization.

In Table II, a certain number of substituted imines are shown which correspond to the general Formula I above in which $R_5$ is an alkyl group; these imines are all new.

TABLE II

[Structure: benzene ring with NH—$R_3$ substituent and $R_1$— substituent, connected to C=N—CH—C(=O)(O$R_5$) with $R_2$ on C and $R_4$ on CH]

| CB No. | $R_1$ | $R_2$ | $R_3$ | $R_4$ | $R_5$ | Example |
|---|---|---|---|---|---|---|
| 4292[1] | Cl | $C_6H_5$ | H | H | $C_2H_5$ | 6 |
| 4361[1] | Cl | $C_6H_5$ | $CH_3$ | H | $C_2H_5$ | 7 |
| 4346 | Cl | $C_6H_5$ | H | $COOC_2H_5$ | $C_2H_5$ | 8 |
| 4362 | Cl | $C_6H_5$ | $CH_3$ | $COOC_2H_5$ | $C_2H_5$ | 9 |
| 4363 | H | $C_6H_5$ | H | H | $C_2H_5$ | 10 |
| 4351 | H | $C_6H_5$ | H | $COOC_2H_5$ | $C_2H_5$ | 11 |
| 4364 | $CH_3$ | $C_6H_5$ | H | H | $C_2H_5$ | 12 |
| 4365 | Cl | n-$C_4H_9$ | H | H | $C_2H_5$ | 13 |

[1]isolated in two stereoisomeric crystalline forms.

I have found that the action of an anhydrous lower aliphatic acid, in particular glacial acetic acid, on either of the two stereoisomeric forms of the substituted imines (I) as well as on mixtures of these two forms leads almost exclusively to the corresponding benzodiazepine. Heating for from several minutes to 1 hour is desirable; after removal of the acid reagent in vacuo and dilution with a suitable solvent, in particular diethyl ether or diisopropyl ether, the benzodiazepine derivative is obtained directly in crystalline state.

Thus, 7-chloro-5-phenyl-2,3-dihydro-1H-benzo[f]-1,4-diazepine (named hereinafter compound A) which has already been described by L. H. Sternbach and E. Reeder (Journal of Organic Chemistry 1961, volume 26, page 4936) may be prepared in two stages, giving an overall yield of 80%, from the unsubstituted imine 4356 CB without having to separate the two steroisomeric forms of the intermediate substituted imine 4292 CB; the N-methyl derivative (B) of compound A, which is already known (see above reference) is obtained in a practically quantitative yield by subjecting the substituted imine 4361 CB for several minutes to the action of acetic acid.

Employing the same technique, the derivatives of compound A substituted on the 3 carbon atoms are obtained. For this purpose, it is sufficient first to react, according to the process of the invention, the free imine 4356 CB with the hydrochloride of a suitably selected α-amino acid ester without isolating the intermediate substituted imine and proceed with the acetic acid treatment in question. For example, using the hydrochlorides of alanine, leucine and methionine as reagents, one obtains the 3-methyl, 3-isobutyl and 3-methylthioethyl derivatives respectively of 7-chloro-5-phenyl-2-oxo-2,3-dihydro 1H-benzo[f]-1,4-diazepine (compounds C, D, E). The yields vary but are always much higher than those indicated in the chemical literature for the same substances (Sternbach, Fryer, Metlesics, Reeder, Sach, Saucy and Stempel, Journal of Organic Chemistry 1962, volume 27, page 3788).

This method has been extended to the preparation of new benzodiazepines carrying a carbalkoxy group on the 3-carbon atom. For this purpose, it is sufficient to treat malonic acid derivatives of products of type (I) such as those indicated in Table II with an aliphatic acid; these derivatives, obtained by the action of a free imine of Formula III on the hydrochloride of an alkyl aminomalonate, may or may not be isolated. However, the yield is particularly high when crystalline substituted imines (I) are reacted in acetic acid.

We have found an advantageous modification for the preparation of benzodiazepines (II) without isolation of the substituted imines (I), which modification is particularly recommended in cases in which the group $R_2$ in the general Formula II denotes a phenyl or substituted phenyl group, $R_3$ is a hydrogen atom and $R_4$ is a carbalkoxy group. Although these substances are easily obtained by the process described above, starting from ketimines III, such as 4356 CB, the yields are somewhat low and the results are difficult to reproduce if the quantity of reactants used is increased, while complete purification of the products by crystallization is, in some cases, laborious. According to this modification, the substituted amino (I) such as 4292 CB is formed by the action of the hydrochloride of an alkyl aminomalonate on the free imine (III) such as 4356 CB, the reaction being carried out in a hydrocarbon solvent, preferably benzene or toluene, while hydrogen chloride gas is passed through the reaction medium to control the cyclization without first isolating the intermediate compound. The resulting benzodiazepine derivative such as 4279 CB is then isolated in the form of the hydrochloride which can subsequently be decomposed into practically pure benzodiazepine.

This improvement is suitable for the preparation of other benzodiazepines having the general Formula II, in particular those mentioned in Table III which may or may not be substituted on the carbon atom in position 3 in the heterocycle. All that is necessary is to replace the hydrochloride of ethyl aminomalonate by the hydrochloride of an alkyl glycinate such as ethyl glycinate which may or may not be substituted on the methylenic carbon atom.

This procedure is recommended for the synthesis in large quantities of compound 4190 CB (Formula II where $R_2$ = cyclohexyl, $R_3$ = H, $R_4$ = H). The use of substituted or unsubstituted amino-malonic esters or amino-acetic esters is not limited to ethyl ester.

The structure of the new carbalkoxy-3-benzodiazepines (II) is obtained not only from the elementary analysis of these compounds but also from a study of their infrared spectra and the results of hydrolysis. The infrared spectra of 3-carbalkoxy benzodiazepine (II) dissolved in methylene chloride have the following features. Vibration bands of the N-H bond of the lactam group without substituent (if this is the case): namely a fine line (free N—H) in the region of 3400 cm.$^{-1}$ and a wide band (attached N—H) in the region of 3200 cm.$^{-1}$. In potassium bromide, the absorption due to N—H is often more complex and may result in the presence of various bands between 3100 and 3400 cm.$^{-1}$; characteristic bands of the ester group at 1730–1755 (>C=O) and in the region of 1200 cm.$^{-1}$ (C—O—C); a characteristic band of a secondary amide at 1660–1700 cm.$^{-1}$ (absence of the amide II band between 1510 and 1550 cm.$^{-1}$); a band at 1590–1610 cm.$^{-1}$ (aromatic >C=C< and >C=N—) flanked by a less intense band at 1560–1580 cm.$^{-1}$ for compounds having two phenyl groups conjugated to >C=N—.

The treatment of 3-carbalkoxy benzodiazepines (II) with a saponifying agent (for example, an alkali metal hydroxide, preferably aqueous or alcoholic potash) and then with a dilute acid reagent (for example, acetic acid), gives rise to hydrolysis and decarboxylation and finally leads to benzodiazepines which are unsubstituted on the 3-carbon atom and, for example, to compound A if compound 4279 CB is put into the reaction, which completely demonstrates the structure proposed. By the treatment of the 3-carbalkoxy benzodiazepines (II) with an alkali such as aqueous or alcoholic potash, then with an alkylating agent such as dimethyl sulphate and thereafter with a dilute acid such as acetic acid, there are obtained the 1-alkylbenzodiazepines, for example, compound B (diazepam) when compound 4279 CB is used. Instead of using the 3-carbalkoxy benzodiazepines (II), the di-salts obtainable by the action of an alkali on the compounds (II) may be treated with an alkylating agent. The action of ammonia or of a primary or secondary amine at room temperature in a suitable solvent such as methanol converts the 3-carbalkoxybenzodiazepines (II) into benzodiazepines carrying an amide function, with or without substituent, in the 3-position.

Nitration of the benzodiazepine derivative 4352 CB in sulphuric acid leads to aromatic derivatives nitrated in the 7-position (cf 4353 CB); the structure is determined by elementary analysis, by the infrared spectrum (nitro bands at 1530 and 1350 cm.$^{-1}$ in potassium bromide) and by its hydrolysis accompanied by decarboxylation which leads to 7-nitro-phenyl-2,3-dihydro-1H-benzo[f]-1,4-diazepine which is already known and has been described by Sternbach, Fryer, Keller, Metlesics, Sach and Steiger in Journal of Medicinal Chemistry 1963, volume 6, page 261.

Reduction of the nitro derivatives, e.g., 4353 CB, for example by catalytic means, leads to the corresponding amino compound carrying a 7-amino group (cf.4354 CB).

The 3-carbalkoxybenzodiazepines (II) generally have a higher melting point than the corresponding benzodiazepines which are unsubstituted on the 3-carbon atom; their solubility in organic solvents is relatively slight.

Table III indicates a certain number of new benzodiazepines (those indicated by a number) carrying a substituent in the 3-position and obtainable by the process of the invention, which are useful as intermediates.

TABLE III

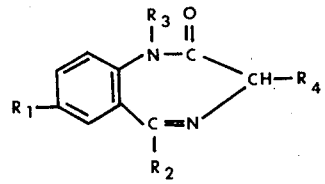

| Name | $R_1$ | $R_2$ | $R_3$ | $R_4$ | Example |
|---|---|---|---|---|---|
| A | Cl | $C_6H_5$ | H | H | 14,15 |
| B | Cl | $C_6H_5$ | $CH_3$ | H | 16 & 55 |
| C | Cl | $C_6H_5$ | H | $CH_3$ | 17 |
| D | Cl | $C_6H_5$ | H | $CH_2$—$CH(CH_3)_2$ | 18 |
| E | Cl | $C_6H_5$ | H | $CH_2$—$CH_2$—$SCH_3$ | 19 |
| 4279 CB | Cl | $C_6H_5$ | H | $COOC_2H_5$ | 20, 21 & 49 |
| 4347 | Cl | $C_6H_5$ | H | $COOCH_3$ | 22 |
| 4366 | Cl | $C_6H_5$ | $CH_3$ | $COOC_2H_5$ | 23 |
| 4348 | Cl | $C_6H_5$ | H | $CONH_2$ | 24 |
| 4367 | Cl | $C_6H_5$ | H | $CONH$—$CH_3$ | 25 |
| 4368 | Cl | $C_6H_5$ | H | $CO$—$N(CH_3)_2$ | 26 |
| 4369 | Cl | $C_6H_5$ | H | $CO$—$NH$—$CH_2$—$CH_2$—$N(C_2H_5)_2$ | 27 |
| 4352 | H | $C_6H_5$ | H | $COOC_2H_5$ | 28 & 50 |
| F | $CH_3$ | $C_6H_5$ | H | H | 29 |
| 4327 | $CH_3$ | $C_6H_5$ | H | $COOC_2H_5$ | 30 |
| 4353 | $NO_2$ | $C_6H_5$ | H | $COOC_2H_5$ | 31 |
| 4354 | $NH_2$ | $C_6H_5$ | H | $COOC_2H_5$ | 32 |
| 4190 | Cl | $C_6H_{11}$ (cyclohexyl) | H | H | 33 & 51 |
| 4370 | Cl | $C_6H_{11}$ (cyclohexyl) | H | $COOC_2H_5$ | 34 |

With a view to obtaining products in a convenient water-soluble form for pharmacodynamic studies and clinical use, we have saponified 3-carbalkoxybenzodiazepines (II) with an alkali metal hydroxide, preferably potassium hydroxide, in an alcoholic medium. A di-metal salt (IV) of the benzodiazepine may be obtained in accordance with the equation given below:

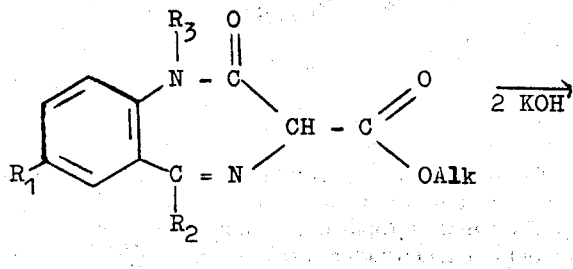

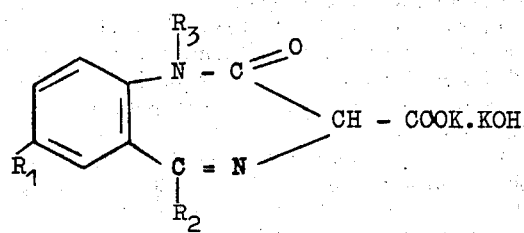

The infrared spectra of compounds IV determined in potassium bromide, agree with the structure, in particular the absence of the >C = O bands (amide, acid or ester) between 1650 and 1750 cm.$^{-1}$, the >C = O band being comprised in the peak around 1600 cm.$^{-1}$, moreover, they show among other things, a very wide and intense absorption band in the region of 3400 cm.$^{-1}$, (vibrational frequencies of N—H of highly chelated NH$_2$) and a wide and complex absorption in the region of 1600–1550 cm.$^{-1}$ (aromatic >C = C<, >C= N—,>C = O of carboxylate ions).

For ease of manipulation, it is best to work in 95 % ethyl alcohol; the temperature should be between room temperature and the boiling point. The purest products are obtained by operating at room temperature. The reaction is accompanied by a transient yellow discoloration. For rapid discoloration, it is advisable to use at least three equivalents of potassium hydroxide. The yield of the "dipotassium salt" is practically quantitative. These dimetal salts (IV); a number of which are given in Table IV below, are colorless powders (with the exception of the nitro and amino derivatives which are yellow), very soluble in water and strongly alkaline in reaction. On acidification, the aqueous solutions give rise to the corresponding benzodiazepines unsubstituted on the 3-carbon atom; thus the compound, 7-chloro-2,3-dihydro-2-oxo-5-phenyl-1H-1,4-benzodiazepine-3-carboxylic acid, monopotassium salt, monopotassium hydroxide becomes benzodiazepine A of Table III.

The same salts (IV) can be obtained by saponification of imines having a double ester function of type I according to the reaction indicated below:

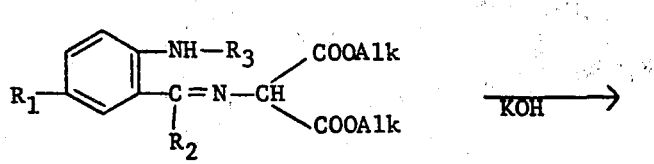

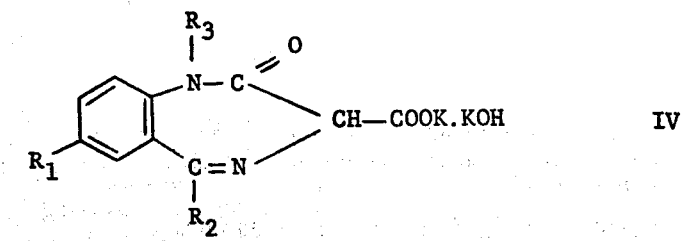

In the case of compound 4306 CB, pharmacodynamic studies confirm the identity of the products obtained by the two methods.

Table IV gives by way of examples, some dipotassium salts prepared according to the process of the invention:

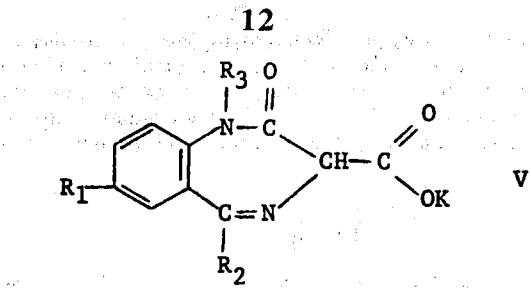

TABLE IV

| CB No. | $R_1$ | $R_2$ | $R_3$ | Example |
|---|---|---|---|---|
| 4306[1] | Cl | $C_6H_5$ | H | 35, 36 & 52 |
| 4350 | Cl | $C_6H_5$ | $CH_3$ | 37 & 38 |
| 4337 | H | $C_6H_5$ | H | 39 |
| 4339 | $CH_3$ | $C_6H_5$ | H | 40 |
| 4335 | $NO_2$ | $C_6H_5$ | H | 41 & 53 |
| 4371 | $NH_2$ | $C_6H_5$ | H | 42 |

[1]The disodium salt and the calcium salt were also prepared, the latter (4372 CB; Example 44) by double decomposition from the dipotassium salt.

By carrying out a reaction under the conditions just described, compound 4348 CB, which has an amide group in the 3-position, gives rise to the corresponding carboxylic derivatives in which the initial amide group is preserved.

To bring about this reaction, it is sufficient to treat an aqueous solution of the product used with a slightly acid reagent at room temperature (that is to say an amount of acid which is just sufficiently strong to liberate the carboxylic function), preferably potassium dihydrogen phosphate or carbon dioxide. The monopotassium salts (V) as a rule crystallize readily provided crystallization is carried out in a sufficiently concentrated solution since they are less soluble in water than the compounds (IV) from which they are derived. They are therefore obtainable in a high yield.

Their formula having been established by elementary analysis, their structure is obtained from the study of their infrared spectra and their chemical properties. The infrared spectra (determined in potassium bromide), agree with the structure V and show, among other things, and in contradistinction to compounds IV, a strong band in the region of 1690 cm.$^{-1}$ due to the

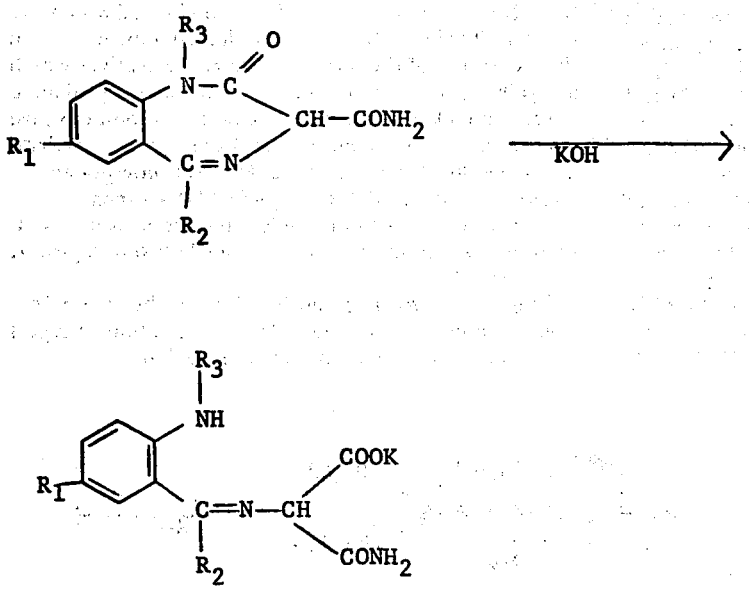

(4349 CB; Example 43)

We have further found that the dimetal salts such as those given in Table IV, may, under very accurate conditions, be converted into the monometal salts ($R_4$ = COOCat). For example, the monopotassium salt of compounds of Formula II are represented by the formula V.

C=O of the cyclic amide; also to be noted is the absence of the amide II band between 1510 and 1550 cm.$^{-1}$ which is characteristic of non-cyclic secondary amides. Only the nitro group, if present, gives a band in this region. Moreover, the vibration of the NH bond of the lactam group manifests itself by two very wide bands in the regions of 3400 cm.$^{-1}$ and 3100 cm.$^{-1}$. Lastly, an intense and complex band in the region of 1600–1620 cm.$^{-1}$ may be attributed to the vibrations of the aromatic C=C and of the >C=N— and of the >C=O of the carboxyl ion.

Aqueous solutions of compounds V generally have a pH in the neutral region. Products V are less stable in aqueous solution than the compounds from which they are derived. The aqueous solutions liberate the corresponding benzodiazepine derivatives unsubstituted on the 3-carbon atom after standing for several hours at room temperature or rapidly upon boiling or in the presence of acetic acid at or above room temperature.

Several potassium benzodiazepine 3-carboxylates (V) are shown in Table V to illustrate this aspect of the invention.

TABLE V

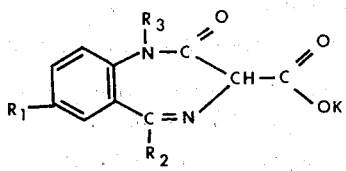

| CB No. | R$_1$ | R$_2$ | R$_3$ | Example |
|---|---|---|---|---|
| 4311 | Cl | C$_6$H$_5$ | H | 45 |
| 4338 | H | C$_6$H$_5$ | H | 46 |
| 4373 | CH$_3$ | C$_6$H$_5$ | H | 47 |
| 4336 | NO$_2$ | C$_6$H$_5$ | H | 48 |

The followng examples illustrate the invention.

EXAMPLE 1

(2-Amino-5-chlorophenyl)-phenyl-methane-imine (4356 CB)

A solution of 228.7 g. (1.5 moles) of 2-amino-5-chlorobenzonitrile in 1800 ml. of dry ether is added slowly in the course of about 3.5 hours to a solution of phenyl magnesium bromide prepared from 109 g. (4.5 gram atoms) of magnesium turnings and 848 g. (5.4 moles) of bromobenzene in 3600 ml. of anhydrous ether, and the mixture is then heated under reflux for 15 hours.

The complex is decomposed by stirring the reaction mixture into a solution prepared from 500 g. of ammonium chloride in 2000 ml. of water to which 3 kg. of crushed ice have been added. After extraction and washing, the ether is evaporated in vacuo at 40° C. The oily residue is taken up in 500 ml. of petroleum ether and left to crystallize by cooling at −20°C. The yellowish crystals formed are dried (309 g.); m.p. 74°C., yield: 92%.

EXAMPLE 2

(2-Methylamino-5-chlorophenyl)-phenyl-methane-imine (4357 CB)

Using the method described in Example 1, but replacing 2-amino-5-chlorobenzonitrile by an equimolecular quantity of 2-methylamino-5-chlorobenzonitrile, compound 4357 CB is obtained in a yield of 61% yellowish crystals; m.p. 97° C. (hexane).

EXAMPLE 3

(2-Aminophenyl)-phenyl-methane-imine (4358 CB)

Proceeding as in Example 1, but replacing the 2-amino-5-chloro-benzonitrile by an equimolecular quantity of 2-amino-benzonitrile, this compound is obtained in a yield of about 80% of crude product. Yellowish crystals are obtained, m.p. 48°C. (isopropyl ether).

EXAMPLE 4

Cyclohexyl-(2-amino-5-chlorophenyl)-methane-imine (4359 CB)

Proceeding as in Example 1, but replacing the bromobenzene by the equimolecular quantity of bromocyclohexane, this compound is obtained in a yield of 81%: Yellowish crystals with double melting point; m.p. 65° C. and then 95° C.

EXAMPLE 5

Butyl-(2-amino-5-chlorophenyl)-methane-imine (4360 CB)

This product is obtained by the technique employed in Example 1 but the bromobenzene is replaced by an equivalent quantity of 1-bromobutane.

A brownish oil is obtained (yield 94%) which is used without purification in subsequent reactions. However, the product may be crystallized in small quantities from cold petroleum ether, m.p. 27°–28°C. (decomposition).

EXAMPLE 6

1-Phenyl-1-(2-amino-5-chlorophenyl)-4-oxo-5-oxa-2-aza-1-heptene (4292 CB)

A mixture of 27.6 g. (0.12 mole) of (2-amino-5-chlorophenyl)-phenyl-methane-imine and 20.7 g. (0.15 mole) of the hydrochloride of ethyl glycine in 150 ml. of methanol is stirred at room temperature for 2.5 hours. A suspension of a pale yellow solid is obtained which consists of the mixture of imine and ammonium chloride formed in the reaction. The solvent is evaporated under reduced pressure and the residue taken up in methylene chloride. It is washed with a 10% aqueous solution of sodium carbonate, then with water, dried over sodium sulphate and the solvent removed by evaporation. A yellow solid remained behind which was crystallized from acetone. 32.4 g. of the crystalline product was obtained; m.p. 130°–135° C; yield 85%.

This product is a mixture of the two stereoisomeric forms and may be used as it is for further reactions.

However, each of these forms can be obtained in the pure state by fractional crystallization from acetone. They have the following melting points: Chelate form, m.p. 148°–150°C.; non-chelate form, m.p. 142°–144°C.; mixing these two forms lowers the melting point.

EXAMPLE 7

1-Phenyl-1-(2-methylamino-5-chlorophenyl)-4-oxo-5-oxa-2-aza-1-heptene (4361 CB)

This compound is prepared by the method indicated in Example 6, the (2-amino-5-chlorophenyl)-phenyl-methane-imine being replaced by the stoichiometric quantity of (2-methylamino-5-chlorophenyl)-phenyl-methane-imine.

On crystallization from hexane, a solid is obtained which consists of a mixture of the two stereoisomeric forms, m.p. 70°–75°C., yield 82%.

This mixture can be used as it is for subsequent reactions. However, each of the two forms can be isolated in the pure state by fractional crystallization from hexane.

The melting points of these two forms are as follows: Chelate form, m.p. 110°C., non-chelate form, m.p. 85°C.

The mixture of the two forms has a considerably lower melting point.

EXAMPLE 8

Diethyl-[2-phenyl-2-(2-amino-5-chlorophenyl)-1-aza-vinyl]malonate (4346 CB)

A solution of 9.2 g. (0.04 mole) of (2-amino-5-chlorophenyl)-phenyl-methane-imine in 16 ml. of absolute alcohol is added dropwise to a boiling solution of 10.6 g. (0.05 mole) of the hydrochloride of ethyl aminomalonate in 30 ml. of absolute alcohol. When this is completed, the mixture is heated under reflux for 30 minutes and the solvent is then evaporated in vacuo.

The residue is taken up in water and in ether, the ethereal solution is decanted, washed with water, dried over sodium sulphate and the solvent evaporated. The product is recrystallized from diisopropyl ether. Yellow crystals are obtained (7.8 g.; yield: 50%, m.p. 106°C.).

EXAMPLE 9

Diethyl[2-phenyl-2-(2-methylamino-5-chlorophenyl)-1-aza-vinyl]-malonate (4362 CB)

This compound is prepared by the method indicated in Example 8, the (2-amino-5-chlorophenyl)-phenyl-methane-imine being replaced by the stoichiometric quantity of (2-methylamino-5-chlorophenyl)-phenyl-methane-imine. The product is a yellow solid, m.p. 88°C. (isopropyl ether). Yield 25%.

EXAMPLE 10

1-Phenyl-1-(2-aminophenyl)-4-oxo-5-oxa-2-aza-1-heptene (4363 CB)

This compound is obtained by the technique described in Example 6, the (2-amino-5-chlorophenyl)-phenyl-methane-imine being replaced by an equimolecular quantity of (2-aminophenyl)-phenyl-methane-imine.

The product is obtained in the form of yellowish crystals, m.p. 106°C. (isopropyl ether); yield: 58%.

EXAMPLE 11

Diethyl[2-phenyl-1-(2-aminophenyl)-1-aza-vinyl]malonate (4351 CB)

Using the same method as described in Example 8, but replacing the (2-amino-5-chlorophenyl)-phenyl-methane-imine by the equimolecular quantity of (2-aminophenyl)-phenyl-methane-imine, compound 4351 CB is obtained in a yield of 31%. Pale yellow crystals are obtained; m.p. 100°C. (diisopropyl ether).

It is to be noted that in this method a small quantity of the cyclized product or 3-carbethoxy-5-phenyl-2-oxo-2,3-dihydro-1H-benzo[f]-1,4-diazepine (4353 CB) can be isolated from the mother liquor in addition to the main product.

EXAMPLE 12

1-Phenyl-1-(2-amino-5-methylphenyl)-4-oxo-5-oxa-2-aza-1-heptene (4364 CB)

This product is obtained by the method described in Example 6, the (2-amino-5-chlorophenyl)-phenyl-methane-imine being replaced by the equimolecular quantity of (2-amino-5-methylphenyl)-phenyl-methane-imine.

Yellowish crystals, m.p. 131°C. (diisopropyl ether); yield: 35%.

It should be noted that the (2-amino-5-methylphenyl)-phenyl-methane-imine which was prepared by the method described in Example 1 by replacing 2-amino-5-chloro-benzonitrile by an equimolecular quantity of 2-amino-5-methylbenzonitrile could not be obtained in the crystalline state. The crude oily product was used in subsequent reactions including the reactions described above.

EXAMPLE 13

1-Butyl-(2-amino-5-chlorophenyl)-4-oxo-5-oxa-2-aza-1-heptene (4365 CB)

This compound is prepared by the method indicated in Example 6, substituting for (2-amino-5-chlorophenyl)-phenyl-methane-imine, an equivalent quantity of butyl-(2-amino-5-chlorophenyl)-methane-imine. Yellow crystals are obtained; m.p. 96°–97°C. (isopropyl ether); yield: 55%.

EXAMPLE 14

7-Chloro-5-phenyl-2-oxo-2,3-dihydro-1H-benzo[f]-1,4-diazepine (A)

The same procedure is employed as in Example 6 and then, without isolating compound 4292 CB, it is taken up in 150 ml. of acetic acid and heating under reflux for 30 minutes. The acetic acid is evaporated until a dry residue is obtained, 250 ml. of diisopropyl ether and 250 ml. of water are added and the mixture then stirred. A yellowish solid separates which is dried and then washed with ether. it is recrystallized from methyl ethyl ketone. Pale yellow crystals are obtained.

First crop 23.4 g., m.p. 214°–216°C. Second crop 2.3 g., m.p. 214°–216°C. Yield: about 80% from the unsubstituted imine. The product is identical with the product described by Sternbach and Reeder, Journal of Organic Chemistry 1961, volume 26, page 4936.

EXAMPLE 15

7-Chloro-5-phenyl-2-oxo-2,3-dihydro-1H-benzo[f]-1,4-diazepine (A)

Acetic acid is added to a solution of 0.409 g. (0.001 moles) of 7-chloro-2,3-dihydro-2-oxo-5-phenyl-1H-1,4-benzodiazepine-3-carboxylic acid, monopotassium salt, potassium hydroxide (4306 CB) in 4 ml. of distilled water to adjust the solution to pH 4. The solution is heated on a water bath for 15 minutes; a solid precipitates which is separated, washed with water and dried; weight 0.216 g; m.p. 214°–216°C; yield 80%. This product is identical with the product obtained in Example 14.

EXAMPLE 16

7-Chloro-1-methyl-5-phenyl-2-oxo-2,3-dihydro-1H-benzo[f]-1,4-diazepine (B)

6 g. of compound 4361 CB are heated under reflux for 15 minutes in 25 ml. of acetic acid. The acetic acid is removed in vacuo and the residue is taken up in water and a little ether. A yellowish solid separates; m.p. 130°C.; the yield is substantially quantitative. It is recrystallized from diisopropyl ether. Yellowish crystals are obtained (4.4 g.); m.p. 132°C.: yield 85% in the first batch. The product is identical with the known product (see reference above in Example 14).

EXAMPLE 17

7-Chloro-3-methyl-5-phenyl-2-oxo-2,3-dihydro-1H-benzo[f]-1,4-diazepine (C)

A mixture of 6.9 g. (0.03 mole) of 4356 CB and 5.1 g. (0.033 mole) of the hydrochloride of the ethyl ester of DL-alanine in 40 cc. of absolute alcohol is heated under reflux for 1 hour. It is evaporated to dryness and the residue taken up in methylene chloride and a 10% sodium carbonate solution. The organic layer is separated, washed with water and dried over sodium sulphate. The solvent is evaporated and the residue taken up in 40 cc. of acetic acid. It is heated under reflux for 5 minutes and the solvent then evaporated under reduced pressure. Diisopropyl ether is added and the product allowed to crystallize; clear yellow crystals are obtained (5.15 g.), m.p. 224°C., yield: 60% in the first crop. The product is identical with that described in Journal of Organic Chemistry 1962, volume 27, page 3788.

EXAMPLE 18

7-Chloro-3-isobutyl-5-phenyl-2-oxo-2,3-dihydro-1H-benzo[f]-1,4-diazepine (D)

The procedure is the same as described in Example 17 except that the hydrochloride of the ethyl ester of DL-alanine is replaced by the hydrochloride of the ethyl ester of DL-leucine in equimolecular quantity. Compound (D) is obtained in a yield of 48%, m.p. 213°C. (ethyl acetate). The product is identical with the product described in the chemical literature (reference given above).

EXAMPLE 19

7-Chloro-3-(3-thiabutyl)-5-phenyl-2-oxo-2,3-dihydro-1H-benzo[f]-1,4-diazepine (E)

This product is obtained utilizing the procedure described in Example 17. The hydrochloride of ethyl ester of DL-alanine being replaced by that of the ethyl ester of DL-methionine. (50% in excess of the theoretical quantity).

Employing the same treatment after crystallization from ethyl acetate, 7-chloro-3-(3-thiabutyl)-5-phenyl-2-oxo-2,3-dihydro-1H-benzo[f]-1,4-diazepine (m.p. 184°C.) is obtained in a yield of 50%. The product is identical with the product described in the chemical literature (reference given above).

EXAMPLE 20

7-Chloro-3-carbethoxy-5-phenyl-2-oxo-2,3-dihydro-1H-benzo[f]-1,4-diazepine (4279 CB)

This compound is obtained by the procedure described in Example 16, compoud 4361 CB being replaced by an equimolecular quantity of compound 4346 CB. Shiny colorless crystals are obtained, m.p. 244°C. (ethyl acetate), yield 74% in the first crop.

EXAMPLE 21

7-Chloro-3-carbethoxy-5-phenyl-2-oxo-2,3-dihydro-1H-benz[f]-1,4-diazepine (4279 CB)

A mixture of 9.2g. (0.04 mole) of compound 4356 CB, 10.6 g. (0.05 mole) of the hydrochloride of ethyl aminomalonate and 5 g. (0.05 mole) of triethylamine in 45 ml. of absolute ethyl alcohol is heated under reflux for 1 hour. The solvent is evaporated under reduced pressure and the residue taken up in water and ether. The ethereal layer is separated, washed with water and dried over sodium sulphate. After evaporation of the solvent, the residue is dissolved in 45 ml. of acetic acid and heated under reflux for 15 minutes. The product is evaporated to dryness under reduced pressure and taken up in ether. A solid separates which is filtered by suction and recrystallized from ethyl acetate. Brilliant, colorless crystals are obtained (6.4 g.) m.p. 244°C., yield: 47%. The product is identical with that obtained in Example 20.

EXAMPLE 22

7-Chloro-3-methoxycarbonyl-5-phenyl-2-oxo-2,3-dihydro-1H-benzo[f]-1,4-diazepine (4347 CB)

A solution of 9.2 g. (0.04 mole) of compound 4356 CB in 20 ml. of methanol is added dropwise, in the course of 1 hour 30 minutes, to a boiling solution of 9.2 g. (0.05 mole) of the hydrochloride of methyl aminomalonate in 30 ml. of methanol. When this is comppleted, heating under reflux is continued for 30 minutes and the product then concentrated to dryness under reduced pressure. The residue is taken up in water and ether, the ethereal layer separated, the product washed with water and dried over sodium sulphate. The solvent is evaporated under reduced pressure. The residue, which consists of the methyl ester homologus with the ethyl ester described in Example 6, could not be obtained in the crystalline state. It is dissolved in 25 ml. of acetic acid, heated under reflux for 15 minutes, the product evaporated to dryness and the residual oil taken up in ether. A colorless solid separates which is filtered by suction and recrystallized from methanol. Colorless crystals are obtained (4.7 g.); m.p. 226°C. A second crop (1.5 g.) is obtained on concentration of the mother liquor; m.p. 222°C.; total quantity 6.2 g., corresponding to a yield of 47%.

EXAMPLE 23

7-Chloro-3-carbethoxy-1-metyl-5-phenyl-2-oxo-2,3-dihydro-1H-benzo[f]-1,4-diazepine (4366 CB)

This product is prepared by the method described in Example 22, the methyl aminomalonate and compound 4356 CB being respectively replaced by ethyl aminomalonate and compound 4357 CB in equimolecular quantities. Light yellow crystals are obtained; m.p. 180°C. (ethyl alcohol); yield 47%.

EXAMPLE 24

7-Chloro-3-carbamoyl-5-phenyl-2-oxo-2,3-dihydro-1H-benzo[f]-1,4-diazepine (4348 CB)

10 g. of 7-chloro-3-methoxycarbonyl-5-phenyl-2-oxo-2,3-dihydro-1H-benzo[f]-1,4-diazepine and 200 ml. of a 13.6% solution of ammonia in methanol are left together overnight at room temperature. The solid rapidly dissolves and after several hours a precipitate gradually forms which increases in quantity with passage of time, until the whole mass has solidified. The solid is filtered by suction and washed with methanol. An additional small quantity of the same product is obtained by concentrating the solution to dryness. The two crops are combined and recrystallized from methanol. Colorless crystals are obtained (7 g.); m.p. 255°–256°C.; yield 74%.

EXAMPLE 25

7-Chloro-3-methylaminocarbonyl-5-phenyl-2-oxo-2,3-dihydro-1H-benzo[f]-1,4-diazepine (4367 CB)

The product is prepared by the method of Example 24, the solution of ammonia in methanol being replaced by the equivalent quantity of a solution of monomethylamine in methanol. Colorless crystals are obtained (ethyl alcohol); m.p. 294°C.; yield 90%.

EXAMPLE 26

7-Chloro-3-dimethylaminocarbonyl-5-phenyl-2-oxo-2,3-dihydro-1H-benzo[f]-1,4-diazepine (4368 CB)

This compound is obtained as in Example 24, the solution of ammonia in methanol being replaced by the equivalent quantity of a solution of dimethylamine in methanol. Colorless crystals are obtained; m.p. 297°C.

EXAMPLE 27

7-Chloro-3-(2-diethylamino-ethylaminocarbonyl)-5-phenyl-2-oxo-2,3-dihydro-1H-benzo[f]-1,4-diazepine (4369 CB)

This compound is obtained by the procedure employed in Example 24, the solution of ammonia in methanol being replaced by a solution of 2-diethylamino-ethylamine (three times the calculated quantity) in 20 times its volume of methanol. Colorless crystals are obtained; m.p. 220°C. (ethyl acetate); yield 90%.

EXAMPLE 28

3-Ethoxycarbonyl-5-phenyl-2-oxo-2,3-dihydro-1H-benzo[f]-1,4diazepine (4352 CB)

This compound is obtained by the method employed in Example 16, compound 4361 CB being replaced by an equimolecular quantity of compound 4351 CB. Colorless crystals are obtained; m.p. 226°C. (ethyl acetate); yield 70% in the first crop.

EXAMPLE 29

7-Methyl-5-phenyl-2-oxo-2,3-dihydro-1H-benzo[f]-1,4-diazepine (F)

The procedure described in Example 14 is employed, compound 4292 CB being replaced by an equivalent quantity of compound 4364 CB.

Yellowish crystals are obtained; m.p. 208°C. (ethyl acetate); yield 44%. This product is identical with that described in the literature (see reference in Example 17).

EXAMPLE 30

7-Methyl-3-ethoxycarbonyl-5-phenyl-2-oxo-2,3-dihydro-1H-benzo[f]-1,4-diazepine (4327 CB)

This compound is obtained by the procedure described in Example 22, the hydrochloride of methyl aminomalonate and compound 4356 CB being replaced by the equivalent quantities of, respectively, the hydrochloride of ethyl aminomalonate and (2-amino-5-methylphenyl)-phenyl-methane-imine prepared according to Example 12.

Yellowish crystals are obtained; m.p. 260°C, yield 25%.

EXAMPLE 31

7-Nitro-3-ethoxycarbonyl-5-phenyl-2-oxo-2,3-dihydro-1H-benzo[f]-1,4-diazepine (4353 CB)

12.3 g. (0.04 mole) of the finely powdered compound 4352 CB are added slowly, with stirring, to 50 ml. of concentrated sulphuric acid (66° Be.) in such a manner that the temperature does not rise above 25°C. 4.8 g. (0.048 mole) of powdered potassium nitrate is then gradually added to the resulting solution at a rate such that the temperature remains below 25°C. When this is completed, the mixture is stirred for 2 hours 30 minutes at room temperature. The reaction mixture is then poured on to a mixture of crushed ice and ether and allowed to stand for 0.5 hour. The solid which separates is filtered by suction, washed with water and with ether. It is recrystallized from a large volume of ethyl acetate. Pale yellow crystals are obtained (7.7 g.), m.p. 271°C.; yield 55%.

EXAMPLE 32

7-amino-3-ethoxycarbonyl-5-phenyl-2-oxo-2,3-dihydro-1H-benzo[f]-1,4-diazepine (4354 CB)

A solution of 4.48 g. (0.0133 mole) of compound 4353 CB dissolved in 80 ml. of dimethylformamide and 120 ml. of ethyl alcohol is hydrogenated at ordinary temperature and pressure in the presence of Raney nickel. The theoretical absorption of hydrogen requires about 3 hours.

After filtration of the catalyst and evaporation of the solvents under reduced pressure, a solid residue is obtained which is recrystallized from a mixture of dimethylformamide and ethyl alcohol. Pale yellow crystals are obtained (3.9 g.); m.p. 305°C. (decomposition); yield: 90%.

EXAMPLE 33

7-Chloro-5-cyclohexyl-2-oxo-2,3-dihydro-1H-benzo[f]-1,4-diazepine (4190 CB)

This product is prepared by the procedure described in Example 17, compound 4356 CB and the hydrochloride of the ethyl ester of DL-alanine being respectively replaced by equimolecular quantities of compound 4359 CB and the hydrochloride of ethyl glycine. Yellowish crystals are obtained: m.p. 210°C. (n-propyl alcohol); yield 71% from the imine. In this case, the intermediate product viz. 1-cyclohexyl-1-(2′-amino-5′-chlorophenyl)-4-oxo-5-oxa-2-aza-1-heptene could not be isolated in the crystalline state.

EXAMPLE 34

7-Chloro-3-ethoxycarbonyl-5-cyclohexyl-2-oxo-2,3-dihydro-1H-benzo[f]-1,4-diazepine (4370 CB)

This product is prepared by the procedure described in Example 22, methyl aminomalonate and compound 4356 CB is respectively replaced by the stoichiometric quantities of ethyl aminomalonate and compound 4359 CB.

Colorless crystals are obtained, m.p. 208°C. (ethyl acetate); yield 40%. It should be noted that in this case, the intermediate diethyl [2-cyclohexyl-2-(2-amino-5-chlorophenyl)-1-azavinyl]-malonate could not be isolated in the crystalline state.

EXAMPLE 35

7-Chloro-2,3-dihydro-2-oxo-5-phenyl-1H-benzo[f]-1,4-diazepine-3-carboxylic acid, monopotassium salt, monopotassium hydroxide (4306 CB)

50 g. of caustic potash are dissolved in 1350 ml. of 96% ethyl alcohol, and 82 g. (0.25 mole) of compound 4347 CB are then added all at once at a temperature of about 70°C.

The solid dissolves rapidly to form a yellow solution which then loses color while simultaneously an abundant colorless precipitate appears.

After cooling, the solid is filtered by suction and washed with alcohol at 96°C. The product is dried at ordinary temperature in a high vacuum. A colorless solid is obtained (quantitative yield), which is completely soluble in water. The aqueous solution is strongly alkaline in reaction; when acidified with acetic acid and heated on a water bath, it yields a precipitate of 7-chloro-5-phenyl-2-oxo-2,3-dihydro-1H-benzo[f]-1,4-diazepine (compound A).

Comments:

1. The preparation may be carried out by replacing compound 4347 CB by the corresponding ethyl ester (4279 CB). A similar yield of compound 4306 CB is obtained.

2. The corresponding sodium salt can be obtained in the same manner by replacing potassium hydroxide by sodium hydroxide.

EXAMPLE 36

7-Chloro-2,3-dihydro-2-oxo-5-phenyl-1H-benzo[f]-1,4-diazepine-3-carboxylic acid, monopotassium salt, monopotassium hydroxide (4306 CB)

2 g. of 4346 CB are added to a solution of 0.84 g. (0.015 mole) of potassium hydroxide in 1 ml. of water and 25 ml. of methanol and the mixture then heated to reflux. The solid dissolves, giving rise to a red solution which rapidly loses its color, a precipitate appearing at the same time. After cooling, the solid is filtered by suction and washed with methanol. A colorless solid is obtained (1.25 g). This compound is found to be identical with that prepared in Example 35.

EXAMPLE 37

7-Chloro-1-methyl-2,3-dihydro-2-oxo-5-phenyl-1H-benzo[f]-1,4-diazepine-3-carboxylic acid, monopotassium salt, monopotassium hydroxide (4350 CB)

This product is obtained by the method described in Example 35, compound 4347 CB being replaced by a stoichiometric quantity of compound 4366 CB. It is a colorless powder which is very soluble in water. Yield: 71%. The aqueous solution is strongly alkaline in reaction.

EXAMPLE 38

7-Chloro-1-methyl-2,3-dihydro-2-oxo-5-phenyl-1H-benzo[f]-1,4-diazepine-3-carboxylic acid, monopotassium salt, monopotassium hydroxide (4350 CB)

The compound may be obtained as described in Example 36, compound 4346 CB being replaced by an equimolecular quantity of compound 4362 CB. It is a colorless powder completely soluble in water and identical with the product of Example 37; yield: 50%.

EXAMPLE 39

2,3-Dihydro-2-oxo-5-phenyl-1H-benzo[f]-1,4-diazepine-3-carboxylic acid, monopotassium salt, monopotassium hydroxide (4337 CB)

This substance is prepared by the method described in Example 35, compound 4347 CB being replaced by a stoichiometric quantity of compound 4352 CB.

Colorless leaflets are obtained which are completely soluble in water and strongly alkaline in reaction; substantially quantitative yield.

EXAMPLE 40

7-Methyl-2,3-dihydro-2-oxo-5-phenyl-1H-benzo[f]-1,4-diazepine-3-carboxylic acid, monopotassium salt, monopotassium hydroxide (4339 CB)

This substance is prepared by the procedure given in Example 35, compound 4347 CB being replaced by an equimolecular quantity of compound 4327 CB. It is obtained in the form of a colorless solid completely soluble in water. The yield is practically quantitative.

EXAMPLE 41

7-Nitro-2,3-dihydro-2-oxo-5-phenyl-1H-benzo[f]-1,4-diazepine-3-carboxylic acid, monopotassium salt, monopotassium hydroxide (4335 CB)

This compound is obtained by the procedure described in Example 35, compound 4347 CB being replaced by an equimolecular quantity of compound 4353 CB. It is a yellow powder which dissolves completely in water and is strongly alkaline in reaction; the yield is substantially quantitative.

EXAMPLE 42

7-Amino-2,3-dihydro-2-oxo-5-phenyl-1H-benzo[f]-1,4-diazepine-3-carboxylic acid, monopotassium salt, monopotassium hydroxide (4371 CB)

This compound is obtained by the method described in Example 35, compound 4347 CB being replaced by a stoichiometric quantity of compound 4354 CB. It is a yellow solid completely soluble in water and having a strongly alkaline reaction. The yield is quantitative.

EXAMPLE 43

Potassium salt of 4-phenyl-4-(2-amino-5-chlorophenyl)-2-carbamoyl-3-aza-3-butenoic acid (4349 CB)

This product is obtained by the method described in Example 35, compound 4347 CB being replaced by an equivalent quantity of compound 4348 CB. Fine yellow crystals completely soluble in water are obtained in quantitative yield.

EXAMPLE 44

7-Chloro-2,3-dihydro-2-oxo-5-phenyl-1H-benzo[f]-1,4-diazepine-3-carboxylic acid, calcium salt (4372 CB)

A solution of 0.55 g. (0.00375 mole) of calcium chloride dihydrate in 5 ml. of water is added to a solution of 1 g. (0.0025 mole) of the dipotassium salt of 7-chloro-2,3-dihydro-2-oxo-5-phenyl-1H-1,4-benzodiazepine-3-carboxylic acid, monpotassium salt, monopotassium hydroxide (4306 CB) in 15 ml. of water. A solid separates out immediately. After it has been left to stand for 10 minutes, it is filtered by suction, then washed with a small quantity of water and finally dried at ordinary temperature in a high vacuum. A yellowish white solid is obtained which is sparingly soluble in water (0.75 g.); yield: 80%.

EXAMPLE 45

7-Chloro-2,3-dihydro-2-oxo-5-phenyl-1H-benzo[f]-1,4-diazepine-3-carboxylic acid, potassium salt (4311 CB)

2.1 g. (0.005 mole) of 4306 CB and 0.68 g. (0.005 mole) of monopotassium phosphate are dissolved at room temperature in 18 ml. of water. Solution proceeds rapidly and then colorless platelets slowly precipitate. The product is filtered by suction, washed first with chilled water and then with absolute alcohol. The product is dried at room temperature for 12 hours and then in a high vacuum. 1.8 g. of colorless crystals completely soluble in water are obtained. The aqueous solution has a substantially neutral reaction; yield 80%. This product is decarboxylated within a few minutes by heating an aqueous solution thereof, compound A being obtained in the crystalline state.

EXAMPLE 46

3-[5-Phenyl-2-oxo-2,3-dihydro-1H-benzo[f]-1,4-diazepine]-carboxylic acid, potassium salt (4338 CB)

This compound is obtained by the procedure described in Example 45 compound 4306 CB being replaced by an equivalent quantity of compound 4337 CB and the volume of water used being reduced by one-half. It is a colorless powder which dissolves in water, giving a substantially neutral reaction; yield: 74%.

EXAMPLE 47

3-[7-methyl-5-phenyl-2-oxo-2,3-dihydro-1H-benzo[f]-1,4-diazepine]-carboxylic acid, potassium salt (4373 CB)

The same procedure is employed as in Example 45, but compound 4306 CB is replaced by compound 4339 CB in stoichiometric quantity and the volume of water used is reduced by one-half.

It is a colorless solid completely soluble in water; yield: 45%.

EXAMPLE 48

3-[7-nitro-5-phenyl-2-oxo-2,3-dihydro-1H-benzo[f]-1,4-diazepine]-carboxylic acid, potassium salt (4336 CB)

This product is prepared by the method of Example 45, compound 4306 CB being replaced by a stoichiometric quantity of compound 4335 CB and the water used is reduced to one-half the volume.

It is a light yellow powder which dissolves in water to give a practically neutral solution; yield: 79%.

EXAMPLE 49

7-Chloro-3-carbethoxy-5-phenyl-2-oxo-2,3-dihydro-1H-benzo[f]-1,4-diazepine (4279 CB)

423.5 g. (2 moles) of the hydrochloride of ethyl amino-malonate and 1250 ml. of dry benzene are placed in a reaction vessel equipped with stirrer, condenser, dropping funnel and immersion tube for the introduction of gaseous hydrogen chloride. The reaction mixture is heated under reflux and a solution of 460 g. (2 moles) of the ketimine (4356 CB) in 1250 ml. of dry benzene is added during the course of 50 minutes. Precipitation of the hydrochloride of the ketimine (4356 CB) in the form of orange-red crystals is observed to begin at the commencement of the introduction of the ketimine. Heating under reflux is continued until the suspended precipitate becomes discolored (ammonium chloride), which takes about 2 hours, and a rapid current of gaseous hydrogen chloride is then bubbled through the reaction mixture for 2 hours while the mixture is kept boiling. The hydrochloride of compound 4279 CB precipitates progressively in the form of an orange powder. The crystals (hydrochloride of 4279 CB and ammonium chloride) are cooled, filtered by suction and rinsed with benzene and ether. To liberate the base, the product is treated with a sodium carbonate solution in the presence of methylene chloride. The organic layer is separated, dried, the solvent evaporated and the residue treated with ether. A practically pure white product is thus obtained (441.5 g.; yield 63.5%); m.p. 243°–244°C.

EXAMPLE 50

3-Ethoxycarbonyl-5-phenyl-2-oxo-2,3-dihydro-1H-benzo[f]-1,4-diazepine (4352 CB)

423.5 g. (2 moles) of the hydrochloride of ethyl aminomalonate and 1250 ml. of benzene are introduced into an apparatus identical with that used in Example 49. The mixture is heated under reflux and a solution of 391 g. (2 moles) of (2-amino-phenyl)-phenyl-methane-imine (4358 CB) in 1250 ml. of dry benzene is added during the course of 50 minutes. From the commencement of addition of the latter, the hydrochloride of compound 4358 CB precipitates in the form of deep red crystals. To facilitate the condensation reaction, 62.5 ml. of methanol, i.e. 2.5% of the total solvent used, are added. The reaction mixture is heated under reflux for 4 hours until decolorization of the precipitate has occurred. The precipitate at the end of the reaction consists solely of ammonium chloride. Methanol is removed by azeotropic distillation (methanol-benzene) and a fast current of gaseous hydrogen chloride is then bubbled through the mixture for two hours while the reaction mixture is kept boiling. The hydrochloride of compound 4352 CB progressively precipitates in the form of an orange powder. The reaction mixture is cooled, the crystals of the hydrochloride of 4352 CB and ammonium chloride are filtered by suction, washed with benzene and with ether. To liberate the base, the hydrochloride is treated in the manner described in Example 49 for the hydrochloride of the compound 4279 CB. 416 g. of practically pure compound 4352 CB are obtained in this way. Yield: 65.5%; m.p. 224°–225°C.

EXAMPLE 51

7-Chloro-5-cyclohexyl-2-oxo-2,3-dihydro-1H-benzo[f]-1,4-diazepine (4190 CB)

The procedure according to Example 49 is employed, the hydrochloride of ethyl aminomalonate being replaced by the stoichiometric quantity of the hydrochloride of ethyl glycinate, compound 4356 CB being replaced by the stoichiometric quantity of compound 4359 CB and benzene by an equal volume of toluene. Compound 4190 CB is finally obtained by decomposition of its orange-red hydrochloride, giving a yield of 66.5%; m.p. 280°C.

EXAMPLE 52

Compound 4306 CB (Formula IV with $R_1 = Cl$, $R_2 = C_6H_5$, $R_3 = H$)

341.5 g. (1 mole) of compound 4279 CB are added as rapidly as possible, with stirring, at 18° to 20°C. to a solution of 224 g. (4 moles) of potassium hydroxide in 5130 ml. of ethyl alcohol containing 10% by volume of water. A clear yellow solution forms after about 2 minutes. Stirring is stopped, crystallization of compound 4306 CB begins after several minutes and is accompanied by progressive decolorization. The product is filtered by suction after 4 hours, washed with absolute alcohol (500 ml.) and then dried to constant weight at 50°C. under an absolute pressure of 0.1 mm. 422 g. of yellowish white leaflets are obtained.

EXAMPLE 53

Compound 4335 CB (Formula IV in which $R_1 = NO_2$, $R_2 = C_6H_5$, $R_3 = H$)

The procedure employed is that described in Example 52, but compound 4279 CB is replaced by an equimolecular quantity of compound 4353 CB. The reaction follows the same course and compound 4335 CB is obtained in the same yield as compound 4306 CB.

EXAMPLE 54

7-Chloro-5-phenyl-2-oxo-2,3-dihydro-1H-benzo-[f]-1,4-diazepine (A)

A suspension of 6.68 g. (0.02 mole) of compound 4279 CB in an aqueous solution of potassium hydroxide (4.5 g of potassium hydroxide in 45 ml. of water) is heated with stirring on a water bath until completely dissolved. There is obtained a strongly yellow colored solution which clears after a few minutes. The hot solution is treated with 6 ml. of acetic acid which causes a pasty product to separate accompanied by evolution of carbon dioxide. Decarboxylation is completed by heating to reflux for a short time. After the reaction is complete, the desired product crystallizes; it is centrifuged, washed with water and dried at 100°C. in vacuo. m.p. 212°C. The yield is practically quantitative. A pure product can be obtained by crystallization as described in Example 14.

Instead of an aqueous solution of potassium hydroxide, a solution of potassium hydroxide in ethyl alcohol, for example a 95% by volume alcohol may be used, the hot solution being treated with acetic acid as described above.

EXAMPLE 55

7-Chloro-1-methyl-5-phenyl-2-oxo-2,3-dihydro-1H-benzo[f]-1,4-diazepine (B)

An aqueous solution prepared by dissolving 7 g. of potassium hydroxide in 15 ml. of water is added to an aqueous solution of 3 g. of compound 4306 CB, then 1.8 g. of dimethyl sulphate is gradually added (about 5 minutes) with stirring, care being taken that the temperature does not rise above 25°C. After the addition is ended, the mixture is left for 2 hours at room temperature, then acidified with acetic acid. A pasty product separates which is covered with diisopropyl ether, and the suspension thus formed is heated to boiling for a few minutes; evolution of carbon dioxide takes place. The product is cooled, diluted with ether and the aqueous phase is separated. Upon evaporation of the solvent, there is obtained a residue which is crystallized from diisopropyl ether. Yield: 80%; m.p. 132°C. The product is identical with the product obtained according to Example 16.

A certain number of the compounds described in the present application have been studied with regard to their action on the central nervous system, as psycholeptics, myorelaxants and tranquilizers. In addition, the acute toxicity has been determined for a number of these compounds.

The study of certain compounds of known pharmacodynamic and clinical activity, such as diazepame and chlorodiazepoxide, has been undertaken under the same experimental conditions, with the same tests and with animals of the same origin as for the new compounds. It has thereby been possible to make quantitative comparisons of the activity of the different compounds for the different tests employed.

In the series of tests briefly described hereafter, each compound was tested with the use of five or six scaled doses on batches of 10 to 20 animals for each dose; it was thereby possible to determine with sufficient exactitude by the method of probits the 50% effective dose (ED 50), that is to say, the dose for which half the animals are protected and react in a predetermined manner according to a particular action.

TESTS EMPLOYED

The following tests were employed:

1. Traction test (mice)

This consists in observing when the treated animals are capable of retrieving a rod grasped by the front paws only. Inability to carry this out was interpreted as a sign of myorelaxant activity.

2. Balance test: rotating rod (mice)

This test consists in observing whether the treated animals are capable of maintaining their balance on a horizontal rod kept in rotation.

Numerous neuroleptic compounds or tranquilizers disturb the equilibration reflex.

3. Anti-convulsant activity (anti-pentetrazole) (mice)

Pentetrazole, injected intraperitoneally in a dose of 125 mg./kg. produces fatal convulsions in 100% of the animals.

Certain compounds exert a protective action preventing convulsions and permitting survival.

4. Anti-convulsant activity (electric shock) (mice)

The test consists in determining the intensity of the electric current required to produce a fatal shock in a batch of test animals.

Certain preventively administered compounds effectively protect a certain percentage of animals subjected to an electric current of an intensity which is fatal to untreated animals.

5. Exploration test (mice)

This extremely simple test consists in placing a mouse at the center of a floor pierced with holes and in noting how many holes the mouse explores in 5 minutes. This test is carried out in a room in which complete silence is observed and which contains no person except the experimenter who is seated and still. It appeals to the curiosity of the animals. The doses of the compounds employed are, however, very small and considerably less than those required to impair movement. This simple test makes it possible to observe whether the compounds assayed produce a more or less pronounced lack of interest in the environment and it gives information which is interesting from the clinical point of view with regard to the treatment of anxiety and restlessness.

6. Spontaneous motor activity in the rat and mouse and provoked motor activity The effect of drugs on voluntary movements of animals can be studied statistically by methods, the details of which will not be discussed here. The mouse, which is an extremely lively animal and moves about a great deal, is particularly suitable for this type of experiment.

Moreover, this spontaneous mobility can be exacerbated by preventive administration to the animals of certain substances such as benzedrine, mescaline and ritaline.

The experimental results obtained by these methods give valuable information for clinical purposes with regard to the treatment of ambulatory psychomotor crises.

7. Antistrychnine activity

This test demonstrates the activity of drugs against a medullary excitant.

8. Morphine excitation

In the cat, morphine produces a specific state of excitation with hallucinations which can be attenuated or suppressed by certain psycholeptic drugs.

In the mouse, the action of morphine is different but also manifested by marked central excitation.

9. Aggressiveness (cat/mouse)

In general, 75 to 80% of cats are aggressive when confronted with white mice. Psycholeptics and tranquilizers may make the cat indifferent and sometimes even amiable to the mouse. Similarly, in the case of cats that are furious and aggressive in relation to humans, diminution or suppression of the instinctive fear and establishment of a climate of confidence are observed.

10. Combativeness

It is possible to make a male rat aggressive towards another male rat enclosed in the same cage by passing an electric current of more or less high voltage through the floor of the cage.

This test, like the preceding one, can obviously give information of clinical value for the treatment of aggression diseases.

11. Conditioning test

The test used consists in educating rats to avoid an electric current passed through the floor of a cage of two compartments when they change compartments. The animal is first warned by a lamp which lights up in the compartment through which the current is passing while the other is in relative darkness.

This test, which requires more or less daily training at the rate of 50 times for each rat, makes it possible to follow the animals and note their progress. The performances realized at the end of a certain time (3 weeks to 1 month of training) are fairly constant, the percentage of errors made by adequately gifted subjects being less than 10 and very often even zero.

One would imagine that disturbances produced in these performances which call upon the memory of animals would be of great importance for the choice of a new medicament. A deconditioning drug of sufficient intensity could have the result of partly depriving the patient of the idea of danger and would consequently require special surveillance of the sick persons.

12. Potentiation of narcosis

Most psycholeptics are hypnotics in large doses, but many of them can, in small doses, without themselves producing any hypnosis, either prolong the time of sleep obtained with a true hypnotic (for example a barbiturate) or appreciably lower the dose of barbiturate required to obtain sleep.

In the attached table are summarized all the results obtained in the different tests briefly recorded above with certain compounds described in the present application, compared with various reference substances of known clinical activity.

TABLE VI

Recapitulating the Activities Obtained with Different Tests
(The figures in the table indicate the 50% efffective doses in mg./kg. and the route of administration: PO = per os; IP = intraperitoneal; SC = subcutaneous; IV = intravenous)

|  | Acute toxicity (M) LD 50 | Traction (M) | Equilibration (M) | Anti-pentetrazole (M) | Electric shock (M) |
|---|---|---|---|---|---|
| Diazepame (compound B) | 720 PO; 220 IP; 800 SC | 1.60 PO | 4.40 PO | 1.7 PO | 5 PO |
| Nor-diazepame (compound A) |  | 3.5 PO | 8.6 PO | 2.9 PO | 9 PO |
| Chlordiazepoxide | 200 PO; 80 IP | 3 PO | 13 PO | 5 PO | 17 PO |
| 4294 CB |  | 20 PO | >20 PO | 20 PO | 100 PO |
| 4279 CB |  | 8 PO | 50 PO | 10 PO | 25 PO |
| 4369 CB |  | >25 PO | >50 PO | >50 PO | >20 PO |

TABLE VI-continued

Recapitulating the Activities Obtained with Different Tests
(The figures in the table indicate the 50% efffective doses in mg./kg. and the route of administration: PO = per os; IP = intraperitoneal; SC = subcutaneous; IV = intravenous)

| | Acute toxicity (M) LD 50 | Traction (M) | Equilibration (M) | Anti-pente-trazole (M) | Electric shock (M) |
|---|---|---|---|---|---|
| 4306 CB | 700 PO; 250 IP | 1.10 PO | 14 PO | 1.7 PO | 4.6 PO |
| Ca 2053 the same formula as 4306 CB but obtained by saponification of the non-cyclic intermediate (4346 CB) | | 1.25 PO | 9.6 PO | 1.7 PO | 3 PO |
| 4350 CB | | 5 PO | >10 PO | 7.5 PO | 20 PO |
| 4335 CB | 560 PO | 1.25 PO | 4.3 PO | 0.44 PO | 3.2 PO |
| 4349 CB | | 10 PO | >10 PO | >10 PO | >10 PO |
| 4311 CB | 870 PO; 310 IP; 450 Sc; 220 IV. | 1.35 PO; 1.75 IP. | 5 PO; 4.5 IP. | 1.65 PO; 2.9 IP. | 2.6 IP |
| 4336 CB | 800 PO | 0.28 PO | 1.5 PO | 0.31 PO | 3 PO |
| 4337 CB | | 5 PO | >10 PO | >10 PO | >10 PO |
| 4338 CB | | 5 PO | >10 PO | >10 PO | >10 PO |
| 4339 CB | | >10 PO | >10 PO | >10 PO | >10 PO |

| | Exploration (M) | Spontaneous motor activity (R) | Spontaneous motor activity (M) | Benzedrine provoked motor activity (R) |
|---|---|---|---|---|
| Diazepame (compound B) | 6 PO | 25 PO | 5 PO | 100 PO |
| Nor-diazepame (compound A) | 7.8 PO | 50 PO | 50 PO | 100 PO |
| Chlordiazepoxide | 20 PO | | | >100 PO |
| 4294 CB | >100 PO | | | |
| 4279 CB | 25 PO | 100 PO | 100 PO | >100 PO |
| 4369 CB | >20 PO | | >10 PO | |
| 4306 CB | 4 PO | <25 PO | 5 PO | >100 PO |
| Ca 2053 the same formula as 4306 CB but obtained by saponification of the non-cyclic intermediate (4346 CB) | 6.25 PO | 25 PO | 10 PO | |
| 4350 CB | 10 PO | | >20 PO | |
| 4335 CB | 1.8 PO | 25 PO | 5 PO | 100 PO |
| 4349 CB | 10 PO | | 10 PO | |
| 4311 CB | 5 IP | 50 PO; 25 IP | 10 PO; 25 IP. | 50 PO |
| 4336 CB | 6 PO | 50 PO | 5 PO | |
| 4337 CB | >10 PO | | | |
| 4338 CB | >10 | | 10 PO | |
| 4339 CB | | | 10 PO | |

| | Benzedrine provoked motor activity (M) | Mescaline provoked motor activity (M) | Ritaline provoked motor activity (M) | Anti-strychnine (M) | Morphine excitation (M) |
|---|---|---|---|---|---|
| Diazepame (compound B) | >20 PO | | | >50 PO | 25 PO |
| Nor-diazepame (compound A) | >20 PO | | | | |
| Chlordiazepoxide | | | | | |
| 4294 CB | | | | | |
| 4279 CB | | | | | |
| 4369 CB | | | | | |
| 4306 CB | >20 PO | 20 PO | 20 PO | 25 PO | 50 PO |
| Ca 2053 the same formula as 4306 CB but obtained by saponification of the non-cyclic intermediate (4346 CB) | | | | | |
| 4350 CB | | | | | |
| 4335 CB | | 20 PO | >20 PO | >20 PO | 50 PO |
| 4349 CB | | | | | |
| 4311 CB | 0 to 20 PO; 0 to 20 IP. | 20 PO | 0 to 20 PO | 20 PO | 20 PO |
| 4336 CB | | | | 25 PO | |
| 4337 CB | | | | | |
| 4338 CB | | | | | |
| 4339 CB | | | | | |

| | Morphine crisis (C) | Aggressiveness (C/M) | Combativeness (R) | Double box conditioning (R) | Narcotic potentation (M) |
|---|---|---|---|---|---|
| Diazepame (compound B) | 25 SC | 25 SC | 25 PO | Without effect | 2.5 PO |
| Nor-diazepame (compound A) | | | 100 PO | Without effect | |

TABLE VI-continued

Recapitulating the Activities Obtained with Different Tests
(The figures in the table indicate the 50% efffective doses in mg./kg. and the route of administration: PO = per os; IP = intraperitoneal; SC = subcutaneous; IV = intravenous)

| | Morphine crisis (C) | Aggressive ness (C/M) | Combativeness (R) | Double box conditioning (R) | Narcotic potentation (M) |
|---|---|---|---|---|---|
| Chlordiazepoxide | 100 SC | | 100 PO | | |
| 4294 CB | | | | | |
| 4279 CB | | | | | |
| 4369 CB | | | | | |
| 4306 CB | 25 SC | 25 SC | <25 PO | Improved performance | 2 PO |
| Ca 2053 the same formula as 4306 CB but obtained by saponification of the non-cyclic intermediate (4346 CB) | | | | | |
| 4350 CB | | | | | |
| 4335 CB | 25 SC | 25 SC | 10 PO | | |
| 4349 CB | | | | | |
| 4311 CB | | | 25 PO; 25 IP | 10 PO | 2 PO |
| 4336 CB | 25 SC | 25 SC | 10 PO | | |
| 4337 CB | | | | | |
| 4338 CB | | | | | |
| 4339 CB | | | | | |

M = mouse;
R = rat;
C = cat

From an examination of the figures given in the table, it is found that

1. The two para-nitro derivatives 4335 and 4336 are extremely active in different tests, especially as myorelaxants and an anticonvulsants in the test for curiosity, on the other hand, they appear to have less effect on the faculties of displacement. Lastly, they have a marked effect in diminishing aggressiveness (test for combativeness).

2. The compound 4306, very similar to 4335, is also highly active and in most of the tests, it is at least equal and frequently superior to diazepame.

3. Compound 4311 is also highly active but slightly less so than 4306. Its activity is slightly less when administered parenterally than when administered orally.

I claim:

1. An ortho-aminoaryl ketimine having the formula

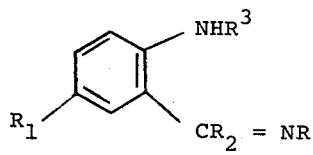

in which R is a group having the formula

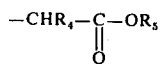

$R_1$ is a hydrogen or halogen atom or a trifluoromethyl, loweralkyl, loweralkoxy, nitro or amino group, $R_2$ is a cyclohexyl, a loweralkyl or a phenyl group, $R_3$ is a hydrogen atom or a loweralkyl group, $R_4$ is a hydrogen atom, lowercarbalkoxy, carbamoyl, N-loweralkylcarbamoyl, N,N-di-loweralkylcarbamoyl, N(di-loweralkylaminoalkyl) carbamoyl, loweralkyl group, and $R_5$ is a loweralkyl group.

2. An ortho-amino-aryl-ketimine having the formula

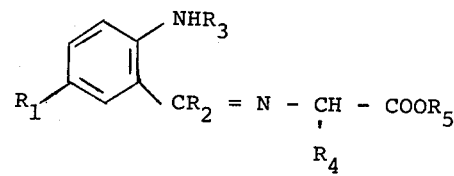

wherein $R_1$ is a hydrogen or chlorine atom or a methyl, nitro or amino group; $R_2$ is a phenyl, n-butyl or cyclohexyl group, $R_3$ is a hydrogen atom or a lower alkyl group, $R_4$ is a hydrogen atom or a carbamoyl, methylcarbamoyl, dimethylcarbamoyl or lower carbalkoxy group and $R_5$ is a lower alkyl group.

3. The compound of claim 2 wherein $R_1$ is chlorine, $R_2$ is phenyl, $R_3$ is hydrogen, $R_4$ is hydrogen and $R_5$ is ethyl.

4. The compound of claim 2 wherein $R_1$ is chlorine, $R_2$ is phenyl, $R_3$ is methyl, $R_4$ is hydrogen and $R_5$ is ethyl.

5. The compound of claim 2 wherein $R_1$ is chlorine, $R_2$ is phenyl, $R_3$ is hydrogen, $R_4$ is —$COOC_2H_5$ and $R_5$ is ethyl.

6. The compound of claim 2 wherein $R_1$ is chlorine, $R_2$ is phenyl, $R_3$ is methyl, $R_4$ is —$COOC_2H_5$ and $R_5$ is ethyl.

7. The compound of claim 2 wherein $R_1$ is hydrogen, $R_2$ is phenyl, $R_3$ is hydrogen, $R_4$ is hydrogen and $R_5$ is ethyl.

8. The compound of claim 2 wherein $R_1$ is hydrogen, $R_2$ is phenyl, $R_3$ is hydrogen, $R_4$ is —$COOC_2H_5$ and $R_5$ is ethyl.

9. The compound of claim 2 wherein $R_1$ is methyl, $R_2$ is phenyl, $R_3$ is hydrogen, $R_4$ is hydrogen and $R_5$ is ethyl.

10. The compound of claim 2 wherein $R_1$ is chlorine, $R_2$ is n-butyl, $R_3$ is hydrogen, $R_4$ is hydrogen and $R_5$ is ethyl.

11. An ortho-aminoaryl ketimine according to claim 2 wherein $R_1$ is hydrogen, chloro, or methyl, $R_2$ is phenyl, $R_3$ is hydrogen or methyl, $R_4$ is hydrogen or $COOC_2H_5$, and $R_5$ is ethyl.

12. A process for producing an N-substituted ortho-aminoaryl ketimine having the formula

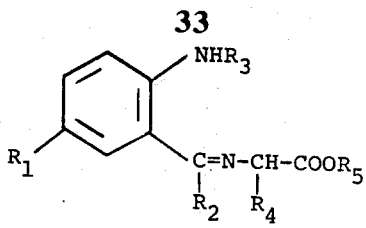

in which $R_1$, $R_2$, $R_3$ and $R_4$ are defined in claim 2 and $R_5$ is a lower alkyl group which comprises reacting an imine having the formula

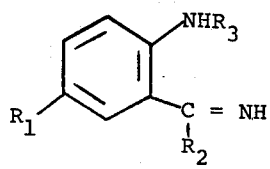

in which $R_1$, $R_2$ and $R_3$ are as above defined, with an aliphatic α-aminocarboxylic acid ester in the form of a base or a salt thereof, having the formula $$H_2N-CHR_4-COOR_5$$

in which $R_4$ is as above defined, and $R_5$ is a lower alkyl group in an inert organic solvent for the imine at a temperature between room temperature and the reflux temperature of the solvent until the said ortho-aminoaryl ketamine is formed.

13. A process according to claim 12 in which the α-aminocarboxylic acid ester is an alkyl α-aminomalonate or an alkyl α-aminoacetate.

* * * * *